United States Patent [19]

Yoshida et al.

[11] Patent Number: 4,931,655
[45] Date of Patent: Jun. 5, 1990

[54] APPARATUS FOR ACCELERATED WEATHER-TESTING OF A SAMPLE USING A METAL HALIDE LAMP

[75] Inventors: Yasuo Yoshida; Tadashi Kakinuma; Tadashi Sakurai, all of Tokyo; Yoshio Kishima; Hirofumi Kinugasa, both of Osaka, all of Japan

[73] Assignees: Iwasaki Electric Co., Ltd., Tokyo; Dainippon Plastics Co., Ltd., Osaka, both of Japan

[21] Appl. No.: 73,303

[22] Filed: Jul. 13, 1987

Related U.S. Application Data

[63] Continuation of Ser. No. 674,842, Nov. 26, 1984, abandoned.

[30] Foreign Application Priority Data

Nov. 30, 1983 [JP] Japan .................. 58-224403
Nov. 30, 1983 [JP] Japan .................. 58-224404

[51] Int. Cl.$^5$ .............................................. H01J 37/32
[52] U.S. Cl. ............................ 250/492.1; 250/504 R
[58] Field of Search ............ 250/492.1, 493.1, 504 R, 250/503.1; 73/150 R, 159

[56] References Cited

U.S. PATENT DOCUMENTS 2,339,906  1/1944  Barnes .................. 313/22

FOREIGN PATENT DOCUMENTS 0895123  1/1945  France .................. 313/22
0018743  4/1983  Japan .
0539344  10/1974  U.S.S.R. ................ 313/22

OTHER PUBLICATIONS

Boxhammer, Die Angewandte Macromolekulare Chemie, vol. 114 (1983), pp. 59–67.
Boxhammer et al., "The Importance of Spectral Distribution and Intensity of Artificial Light Sources in UV and IR Region of Radiation for Accelerated Ageing of Polymers," Die Angewandte Macromolekulare Chemie, vol. 137 (1985), pp. 15–27.

*Primary Examiner*—Bruce C. Anderson
*Attorney, Agent, or Firm*—Shapiro and Shapiro

[57] ABSTRACT

Prior to weathering test for samples, of example, plastic, fiber, or paint, the samples are exposed to ultraviolet ray radiation emitted from high pressure metal halide vapor discharge lamp at an energy level capable of deteriorating the samples in a short time, while maintaining the samples at a temperature which can not be a cause of the deterioration. According to the deterioration level, samples to be subjected to the weathering evaluation test are selected.

6 Claims, 5 Drawing Sheets

APPARATUS FOR ACCELERATED WEATHER-TESTING OF A SAMPLE USING A METAL HALIDE LAMP

This is a continuation application of Ser. No. 674,842 filed Nov. 26, 1984, which is now abandoned.

BACKGROUND OF THE INVENTION

1. Field of the Invention

The present invention relates to a pre-testing method and apparatus for a weathering test of a sample of plastic, fiber, coating material, or the like.

2. Description of the Prior Art

Conventionally, in measurement of weather-ability of plastic material or the like in Japan and elsewhere, weathering machines according to Japanese Industrial Standard B7751 to 7754 are generally used.

In these testing machines, ordinarily, a light source such as a carbon arc lamp, xenon arc lamp or the like is used and the light emitted from this light source is irradiated onto a sample, thereby performing the accelerated weathering test.

However, in an apparatus using such a light source which is employed in those weathering machines, an ultraviolet irradiation intensity is generally about 6 mW per 1 $cm^2$ of the surface to be irradiated, so that it takes approximately hundreds of hours or longer to measure and discriminate the ultraviolet deterioration characteristic that equivalently corresponds to a one-year irradiation by solar light.

Also, conventionally, a method whereby samples for every lot are subjected to one hundred percent (100%) test is generally carried out, so that it takes a long time for measurement and discrimination of the result, and this method is extremely inefficient.

SUMMARY OF THE INVENTION

It is an object of the present invention to provide a pre-testing method and apparatus for allowing the weathering test to be very efficiently performed.

For this purpose, according to the invention, samples which will be subjected to the weathering test are maintained at such a temperature that it does not become a major cause for heat deterioration, and in this state ultraviolet rays having such an energy level as to deteriorate the samples in a short time are irradiated onto the samples, thereby selecting a sample that should be subjected to the weathering test in accordance with the degree of deterioration.

The use of the pre-testing method according to the invention makes it possible to certainly determine a tendency and degree of ultraviolet deterioration characteristic of the sample in an extremely short time. Therefore, if the sample which should be tested by the weathering machine is pre-selected on the basis of this result, there will be no need to permit the sample to be subjected to the 100% test. Thus, there is an advantage such that the test can be remarkably efficiently executed. Also, the testing apparatus for use in the pre-test according to the invention has a simpler structure than the weathering machine and is economical. Consequently, the advantage of reduction of the test time due to the execution of this pre-test greatly exceeds the economic disadvantage of the cost of the pre-testing apparatus.

DETAILED DESCRIPTION OF THE PREFERRED EMBODIMENT

An embodiment of the present invention will now be described. First, necessary samples are produced for every lot.

Next, the ultraviolet rays having an intensity of 50 mW or more per 1 $cm^2$ of the surface to be irradiated are irradiated onto these samples by a light source combination of a high pressure metal vapor electric discharge lamp and a filter which transmits only the ultraviolet rays within a wavelength range of 300 to 400 nm under the condition whereby the temperature of the sample becomes 80° C. or less. The reasons why the wavelength range of the ultraviolet rays is specified by the above-mentioned range are as follows. Namely, the test conditions specified by the Japanese Industrial Standard rule are not satisfied by a wavelength range less than 300 nm, strictly speaking, below 275 nm. On the contrary, with a wavelength range over 400 nm, a significant amount of visible and infrared rays are included in the light that is irradiated from the light source, so that the sample will have been largely thermally affected. Therefore, it is necessary to avoid such influence, and the like.

Figure 1:
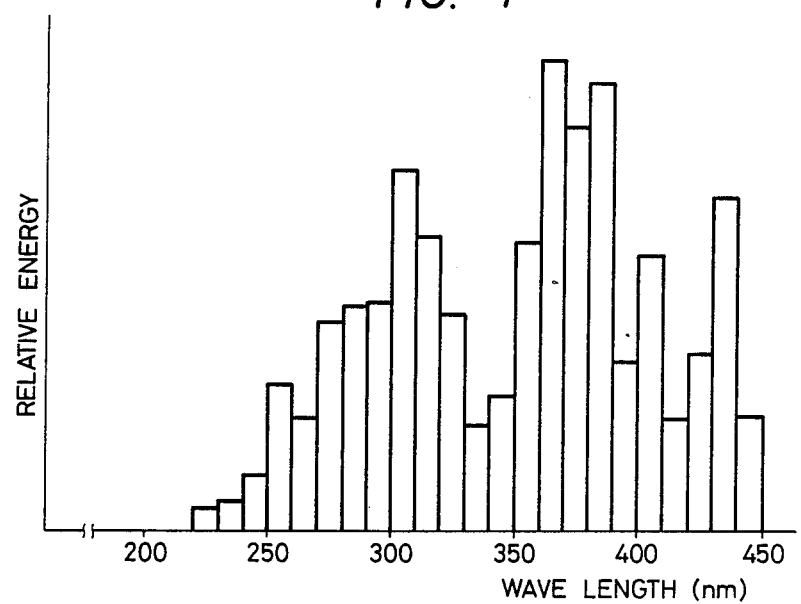
FIG. 1 shows a spectral energy distribution diagram of a metal halide lamp for an ultraviolet light source which is used in the present invention.

Although the higher irradiation intensity of the ultraviolet rays to a sample is preferable, a desirable range is approximately 80 to 200 mW per 1 $cm^2$ of the surface to be irradiated from the economical viewpoint of the apparatus, preferably, about 100 to 150 mW. The optimum high pressure metal vapor discharge lamp to obtain such wavelength range and intensity is set forth in, for example, Japanese Patent Application Publication Laid-open No. 18743/1983. This lamp is what is called a metal halide lamp in which a halide of as iron and tin, for example, is enclosed together with proper quantities of mercury and rare gas in a light emitting tube made of quartz glass having at least a pair of electrodes. The light emission spectrum of this metal halide lamp when it is lit has a fairly large energy distribution in the wavelength range of 300 to 400 nm as shown in FIG. 1. This metal halide lamp is not limited to a lamp wherein the halide of iron and tin is added to the light emitting tube but may be a lamp wherein metal halide mainly containing halide of iron is enclosed in the light emitting tube.

As a lamp having are energy peak in the wavelength range of 300 to 400 nm, there is known a carbon arc lamp which has been used in a weathering machine. However, this lamp irradiates a significant amount of infrared rays as well as the ultraviolet rays, and at the same time gases such as CO, $CO_2$, NO, $NO_2$, etc. are generated while the lamp is lighting. Therefore, as disclosed in, e.g., Japanese Utility Model Application Publication Laid-open No. 16796/1977, the lamp itself has to be equipped with cooling and ventilating mechanisms, causing the lamp and overall apparatus to become complicated and to be increased in size and cost. Thus, this type of lamp is quite improper for implementation of the present invention.

Even in using the foregoing metal halide lamp, it is impossible to avoid the irradiation of energy in a wavelength range other than 300–400 nm, so that it is necessary to restrict the wavelength range of light which is irradiated to 300–400 nm by use of a combination with a proper filter. The optimum filter which is used for this purpose is a filter made of soft glass having a low melting point which consists of, for instance, $SiO_2$ of 60–65% (percentage by weight, hereinafter), Pb of 15–20%, Na of 7–8%, K of 7–8%, Co of 1%, and Ni of 1%.

Figure 2:
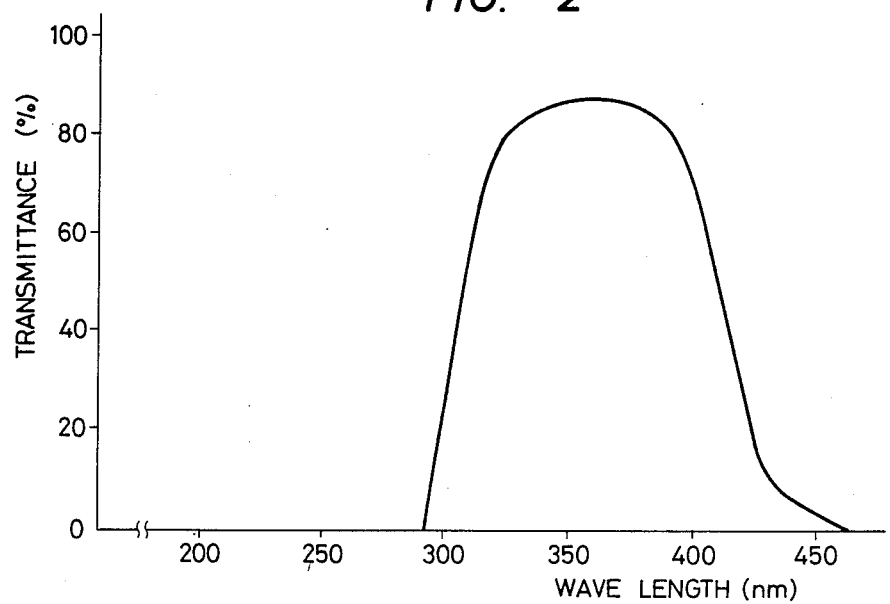
FIG. 2 shows a transmission characteristic diagram of a filter which is used in combination with the metal halide lamp.
Figure 3A:
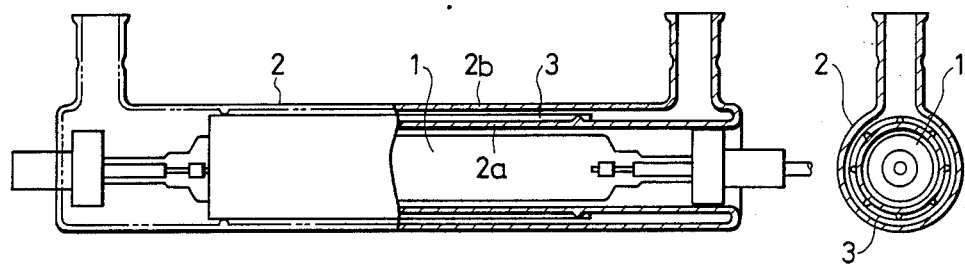
FIGS. 3A and 3B illustrate a front view and a side elevational view of the light source combination of the metal halide lamp and filter, respectively.
Figure 3B:
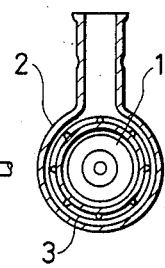

The ultraviolet transmission characteristic of this filter is as shown in FIG. 2. By combining this filter with the above metal halide lamp, the ultraviolet rays of wave lengths 290 to 460 nm, particularly 300 to 400 nm can be extremely efficiently obtained. However, if this filter is merely attached around the metal halide lamp, the filter will break immediately due to the radiation heat from the lamp. Therefore, for example, as shown in FIGS. 3A and 3B, a water cooled light source 6 is suitably constituted in a manner such that: a water cooled jacket 2 has an inner tube 2a and an outer tube 2b which consist of quartz glass which can transmit the ultraviolet rays; a cooling liquid is circulated between the inner and outer tubes 2a and 2b; a light emitting tube 1 is arranged at the center of the inner tube 2a of the water cooled jacket 2; and a filter 3 is disposed between the inner and outer tubes 2a and 2b.

In Japanese Utility Model Application Publication Laid-open Nos. 29675/1977 and 29034/1979, there are disclosed apparatuses such that, in a weathering machine, the ultraviolet rays in a particular wavelength range of, e.g., 300–400 nm are controlled by combining a filter with a lamp. However, in both such apparatuses, the radiation energy of the lamp varies depending upon the elapse of time from the lighting of the lamp and upon a change in power source voltage, so that the energy components in a particular wavelength range also change; therefore, in order to always make those energy components constant, the energy change in the particular wavelength range is detected, thereby controlling a voltage which is applied to the lamp in accordance with that change. Consequently, the above-mentioned apparatuses are quite different from the apparatus of the invention wherein the light emitted from the lamp is simply irradiated onto the sample through the filter.

Figure 4A:
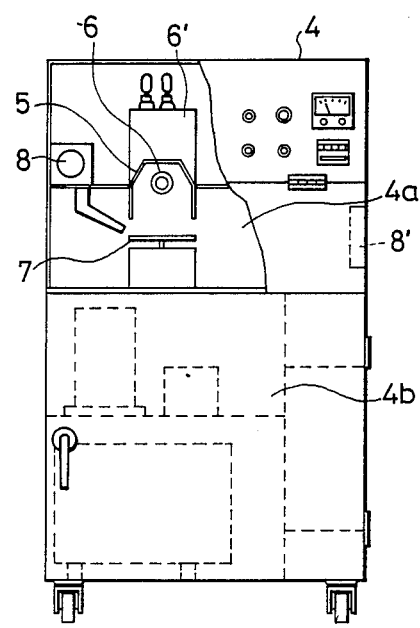
FIGS. 4A and 4B illustrate a front view and a side elevational view of a pre-testing apparatus for use in the present invention, respectively.
Figure 4B:
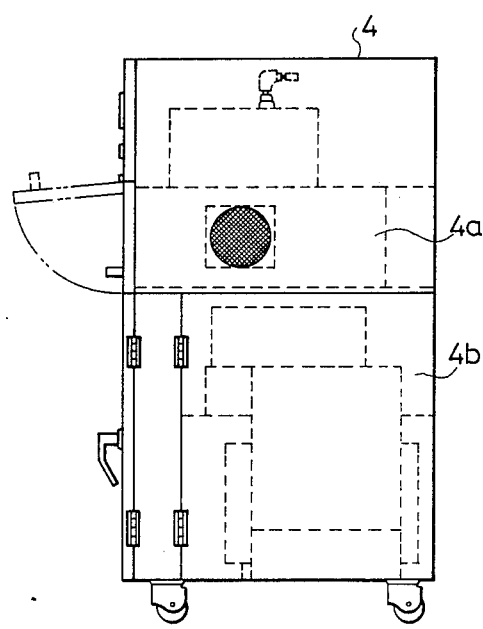

FIGS. 4A and 4B illustrate a front view and a side elevational view of an example of a testing apparatus to implement the present invention. In the drawings, reference numeral 4 denotes a testing apparatus main body; 4a is an ultraviolet irradiating chamber; and 4b is a chamber for enclosing attached apparatuses. A light source apparatus 6' is provided over the ultraviolet irradiating chamber 4a. The light source apparatus 6' comprises a reflecting mirror 5 and the light source 6 such as a metal halide lamp or the like attached in the apparatus 6'. A sample mounting plate 7 is disposed below the light source 6 so as to be vertically adjustable and rotatable as necessary. The distance between the sample mounting plate 7 and the light source 6 can be adjusted by vertically moving either of or both of the sample mounting plate 7 and the light source apparatus 6'.

The reason why the testing apparatus is constituted in this way is to eliminate a variation in distance between the sample and the light source 6 due to the capacity of the light source 6, thickness of sample, etc. By suitably selecting the capacity of the light source 6 and the distance between the light source 6 and the sample, it is possible to irradiate onto the sample the ultraviolet rays having an intensity of 50 mW or more per 1 $cm^2$, preferably, 80 to 200 mW, and more desirably, 100 to 150 mW. In order to uniformly irradiate the ultraviolet rays onto the sample, the sample mounting plate 6 can be freely rotated as necessary.

A cooling airstream is sent toward the sample mounting plate 7 by an air blower 8 and the air in the ultraviolet irradiating chamber 4a is exhausted to the outside by an air exhausting apparatus 8'. When irradiating the strong ultraviolet rays as mentioned above onto the sample, it is necessary to maintain the sample at temperatures below about 80° C. for prevention of deformation of the sample due to the heat. However, as mentioned above, this temperature can be easily controlled by using the water cooled metal halide lamp as the light source in combination with the filter and also by cooling the sample by use of the air blowing and exhausting apparatuses, and the like. Table 1 shows the ultraviolet irradiation time and the temperature of the sample when the surface of the sample is irradiated by the ultraviolet rays of a constant intensity in the cases where: only the water cooled metal halide lamp is used (no filter); the filter is combined with this lamp (filter is used); and the means for cooling the sample is also used in addition to the filter (filter and sample cooling means are used), respectively.

TABLE 1

| Ultraviolet rays irradiation intensity (mW/$cm^2$) | No filter | Filter is used. | Filter and sample cooling means are used. |
|---|---|---|---|
| 20–60 | For one hour and at 100° C. or over | For ten hours and at 100° C. or over | For 100 hours or more and at 65° C. or below |
| 80–120 | For 0.3 second and at 100° C. or over | For one hour and at 100° C. or over | |

As will be obvious from this table, in the case where the filter is combined with the water cooled metal halide lamp and the sample cooling means is also utilized, even if the strong ultraviolet rays having an intensity of 80 to 120 mW/$cm^2$ are irradiated onto the sample for more than hundred hours, the sample can be maintained at temperatures of 65° C. or below.

The cooling of the sample can be also controlled by control of the input to the lamp or the temperature of the sample mounting plate in addition to the control of the quantity and temperature of the cooling air. Further, a pump, cooler and the like for the cooling water to the light source are enclosed in the chamber 4b for enclosing the attached apparatus in addition to a power supplying apparatus, ballast apparatus and the like for the light source.

In such a testing apparatus as described above, for example, in the case where the metal halide lamp of the rated input of 1.5 kW was used as the metal halide lamp of the light source and the distance between the light source 6 and the sample mounting plate 7 was set to 10 cm and the light source 6 was lit by the rated input, the ultraviolet irradiation intensity on the sample mounting plate 7 is about 100 mW per 1 cm². This value is approximately 10 to 15 times larger than the ultraviolet irradiation intensity of a conventional weathering machine. When it is assumed that the ultraviolet deterioration characteristic of the sample when such strong ultraviolet rays are irradiated onto the sample has a similar tendency to the ultraviolet deterioration characteristic of the sample tested by the actual weathering machine, it is possible to discriminate the ultraviolet deterioration characteristic for a time interval that is about 1/10–1/15 shorter than the time interval that will be needed in the case where the weathering machine is used.

As described above, the use of the foregoing method enables the ultraviolet deterioration characteristics of samples for every lot to be discriminated in an extremely short time. Therefore, if samples are selected from among these samples in accordance with a degree of ultraviolet deterioration and are tested by the weathering machine, unnecessary tests and testing time can be eliminated, so that the test becomes very efficient.

The largest problem in adopting the testing method according to the invention relates to whether or not the ultraviolet deterioration characteristic of the sample when strong ultraviolet rays are irradiated according to the invention presents the same tendency as the ultraviolet deterioration characteristic of a sample which is tested by the weathering machine. This is because unless they present the same tendency, the pre-testing method according to the invention will be meaningless. Therefore, as shown in the following examples, many samples consisting of various kinds of plastic materials were tested by the testing apparatus (hereinafter, referred to as the pre-testing apparatus) to implement the invention and by the weathering machine (hereinafter, referred to as the formal testing machine), and the tendency and degree of the ultraviolet deterioration were examined. The testing apparatus and machine used in each example and the test conditions are as follows.

(1) PRE-TESTING APPARATUS

Model

The apparatus made by Iwasaki Electric Co., Ltd. (with a structure as shown in FIGS. 4A and 4B)

Conditions

Lamp used: Metal halide lamp of 1.5 kW Radiation wavelength: 300–400 nm

Energy distribution: As shown in FIG. 1 Ultraviolet irradiation intensity on the surface of the sample: 100±5 mW/cm²

The highest temperature at the sample surface: 65° C. or less

(2) FORMAL TESTING MACHINE

Model

WE-SUN-HC made by Toyo Electrochemical Industry Co., Ltd. (testing machine which is used in the testing method based on Japanese Industrial Standard A1415)

Conditions

Lamp used: Carbon arc lamp of 4 kVA

Ultraviolet irradiation intensity on the surface of the sample: 6 mW/cm²

Black panel temperature: 63±3° C.

Spray: 18 min/120 min

Also, in this test, the tendency and degree of the ultraviolet deterioration were examined from the changes in color difference and physical property of the sample which had been tested by the above testing apparatus and machine. A discriminating method and the test result in the practical example with regard to each of the color difference test and physical property test will now be explained hereinbelow, respectively.

In the following examples, typical plastic materials were selected as samples and they were tested under the particular conditions as mentioned above. The invention is not limited to these examples.

((A)) COLOR DIFFERENCE TEST

With respect to the samples at every time obtained by the above two testing apparatus and machine, the whole color differences before and after the test were obtained and they were plotted in a graph in which an axis of abscissa indicates the time and an axis of ordinate represents the color difference. Each time at the same color difference was read and the ratios of the times regarding the formal testing machine and pre-testing apparatus were obtained. Then, the magnifications of the ultraviolet deterioration accelerating properties were derived. For the whole color difference, ΔE (color difference) was obtained from CIEL* a* b* which is the colorimetric system on the basis of the International Illumination Committee in 1976. As the color difference meter, CR-100 made by Minolta Camera Co., Ltd. was used.

EXAMPLE 1

Sample: Hard transparent PVC sheet containing organic tin. The thickness is 0.4 mm. The stimulus values of the XYZ system which is the colorimetric system on the basis of the International Commision on Illumination in 1931 are X, Y and Z, while the chromaticity coordinates are x and y, namely.

$$x = \frac{X}{X + Y + Z}$$

$$y = \frac{Y}{X + Y + Z}$$

In this example, the reference color is set such that Y=47.4, x=0.307 and y=0.311, wherein, behind the sample, a white sheet is placed.

Figure 5A:
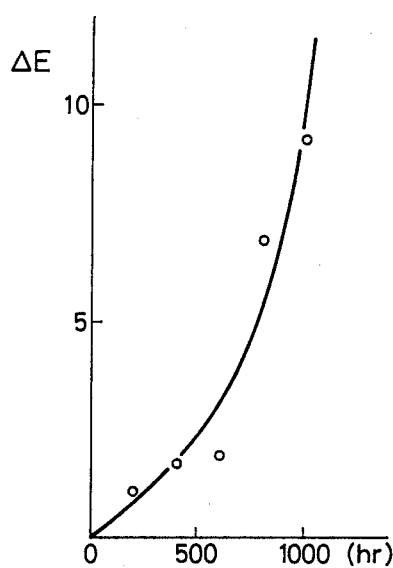
FIGS. 5 to 10 show comparison diagrams between the test result in examples of the invention and the test result by a conventional method.
Figure 5B:
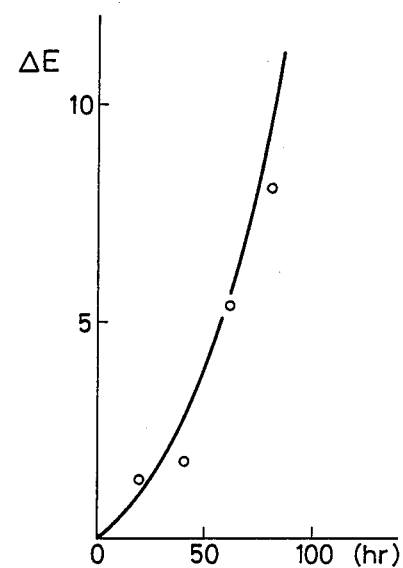

Result: In case of the formal testing machine .... As shown in FIG. 5A. In Case of the pre-testing apparatus .... As shown in FIG. 5B.

Comparison: As shown in Table 2 (mean magnification: 12.7).

TABLE 2

| ΔE | Formal testing machine R (hours) | Pre-testing apparatus P (hours) | R/P |
| --- | --- | --- | --- |
| 2.0 | 450 | 35 | 12.9 |
| 4.0 | 700 | 51 | 13.7 |
| 8.0 | 920 | 76 | 12.1 |

TABLE 2-continued

| ΔE | Formal testing machine R (hours) | Pre-testing apparatus P (hours) | R/P |
|---|---|---|---|
| 10.0 | 1000 | 84 | 11.9 |

(Mean: 12.7)

As will be obvious from the above experiment example, the use of the pre-testing apparatus according to the invention enables the data regarding the ultraviolet deterioration of the sample to be always derived in a short time as compared with the case where the formal testing machine was used. The ratio of the test times was approximately thirteen. This result nearly coincides with the prediction value calculated from the difference in ultraviolet irradiation intensity per 1 cm$^2$ of the surface to be irradiated. Thus, it was confirmed that the ultraviolet deterioration characteristic of the sample in the case where the pre-testing apparatus according to the invention was used has substantially the same tendency as that in the case where the sample was tested by the formal testing machine. In addition, the sample was maintained at a temperature below about 65° C. during the test and even in case of hard vinyl chloride or the like, there was no deformation or the like due to the heat.

EXAMPLE 2

Sample: ABS sheet (Grade: A-322 made by Toray Industries, Inc., Natural). The thickness is 2.0 mm. (Reference color: Y=62.5, x=0.328, y=0.342)

Figure 6A:
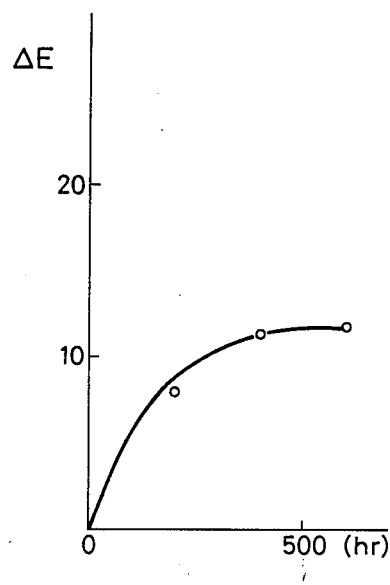
Figure 6B:
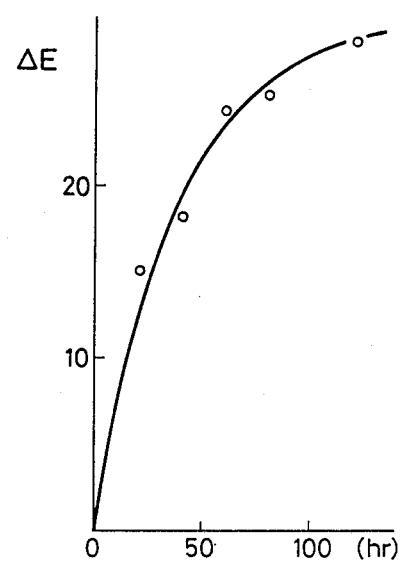

Result: In case of the formal testing machine . . . . As shown in FIG. 6A. In case of the pre-testing apparatus . . . . As shown in FIG. 6B.

Comparison: As shown in Table 3 (mean magnification: 15.4).

TABLE 3

| ΔE | Formal testing machine R (hours) | Pre-testing apparatus P (hours) | R/P |
|---|---|---|---|
| 2.0 | 30 | 2 | 15.0 |
| 4.0 | 70 | 5 | 14.0 |
| 8.0 | 160 | 11 | 14.5 |
| 10.0 | 270 | 15 | 18.0 |

(Mean: 15.4)

EXAMPLE 3

Sample: Acrylic denaturation PVC sheet (Trade name: Daipla AV sheet). The thickness is 3.0 mm. (Reference color: Y=73.7, x=0.320, y=0.319)

Figure 7A:
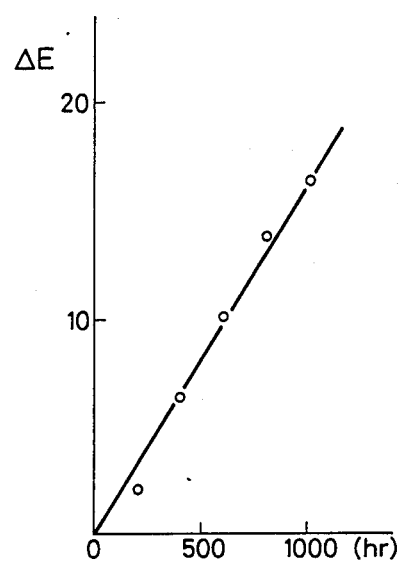
Figure 7B:
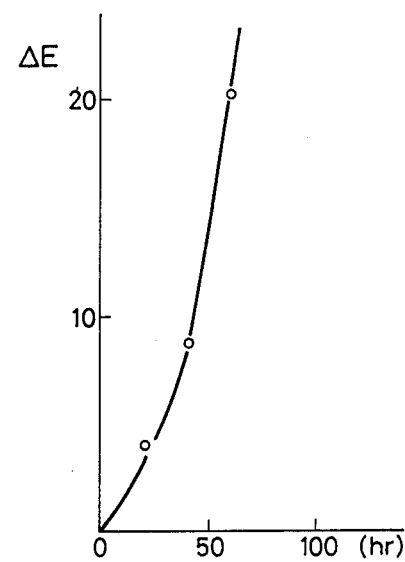

Result: In case of the formal testing machine . . . . As shown in FIG. 7A. In case of the pre-testing apparatus . . . . As shown in FIG. 7B.

Comparison: As shown in Table 4 (mean manification: 14.3).

TABLE 4

| ΔE | Formal testing machine R (hours) | Pre-testing apparatus P (hours) | R/P |
|---|---|---|---|
| 4.0 | 250 | 25 | 10.0 |
| 8.0 | 480 | 38 | 12.6 |
| 12.0 | 740 | 47 | 15.7 |
| 16.0 | 1000 | 53 | 18.9 |

(Mean: 14.3)

EXAMPLE 4

Sample: Polycarbonate (Trade name: Daipla Double Skin sheet PD-600). The thickness is 6.0 mm. (Reference color: Y=34.9, x=0.314, y=0.317)

Figure 8A:
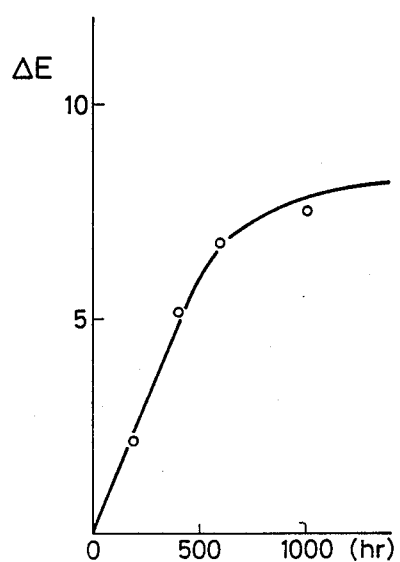
Figure 8B:
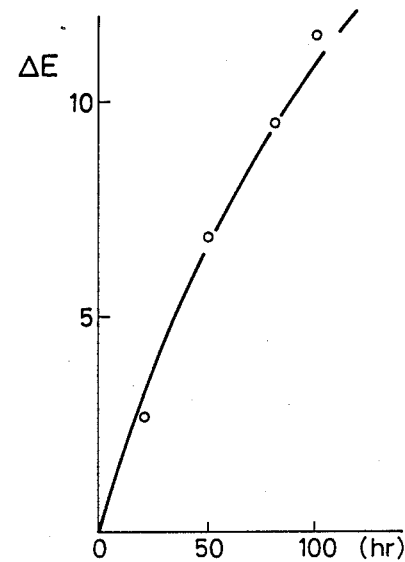

Result: In case of the formal testing machine . . . . As shown in FIG. 8A. In case of the pre-testing apparatus . . . . As shown in FIG. 8B.

Comparison: As shown in Table 5 (mean magnification: 13.8).

TABLE 5

| ΔE | Formal testing machine R (hours) | Pre-testing apparatus P (hours) | R/P |
|---|---|---|---|
| 2.0 | 160 | 12 | 13.3 |
| 4.0 | 320 | 27 | 11.9 |
| 6.0 | 500 | 43 | 11.6 |
| 8.0 | 1150 | 63 | 18.3 |

(Mean: 13.8)

EXAMPLE 5

Sample: Polyethylene sheet (Grade: Hizecks 5000SF made by Mitsui Petrochemical Industries, Ltd.). The thickness is 0.5 mm. (Reference color: Y=57.2, x=0.305, y=0.309)

Figure 9A:
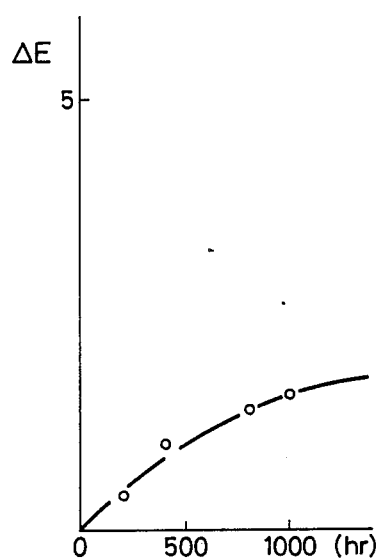
Figure 9B:
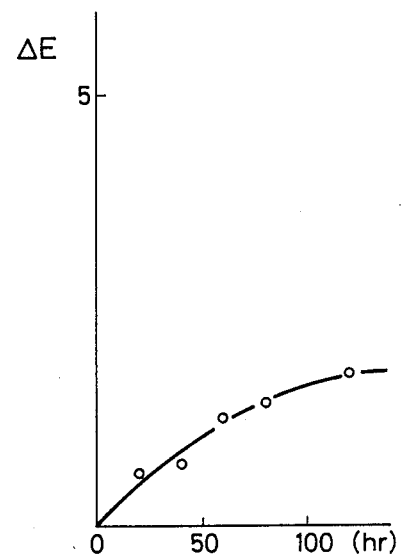

Result: In case of the formal testing machine . . . . As shown in FIG. 9A. In case of the pre-testing apparatus . . . . As shown in FIG. 9B.

Comparison: As shown in Table 6 (means magnification: 10.3).

TABLE 6

| ΔE | Formal testing machine R (hours) | Pre-testing apparatus P (hours) | R/P |
|---|---|---|---|
| 0.5 | 220 | 22 | 10.0 |
| 1.0 | 500 | 48 | 10.4 |
| 1.5 | 920 | 88 | 10.5 |

(Mean: 10.3)

As will be obvious from the comparison data in Examples 1 to 5, the use of the pre-testing method according to the invention enables the data regarding the ultraviolet deterioration of the sample to be always obtained in a short time as compared with the case where the formal testing machine was used. The ratio of the test times was about 10 to 20 and the mean value was about 15. This result almost coincides with the prediction values calculated from the difference in ultraviolet irradiation intensity per 1 cm$^2$ of the surface to be irradiated. Thus, it was confirmed that the ultraviolet deterioration characteristic of the sample in the case where the testing method according to the invention was used has substantially the same tendency as that in the case where the sample was tested by the formal testing machine. The reason why there is the difference in acceleration of the ultraviolet deterioration in dependence upon the kinds of plastic materials is because the absorption characteristics of the ultraviolet rays differ due to the molecular structures and first hues of the plastic materials. On the other hand, there is a tendency such that the magnification also becomes large with an increase in ΔE. It can be considered that this is because no water is used in the pre-testing apparatus which is used in the present invention, so that a degree of stain on the surface of the sample is less than that in the case where the formal testing machine was used and therefore the ultraviolet deterioration was accelerated.

((B)) PHYSICAL PROPERTY TEST (B-1) Bending test at a bend angle of 180°

After the ultraviolet rays had been irradiated onto the portion of 30 mm² of the central portion of the sample having a width of 10 mm and a length of 65 mm by the formal testing machine and by the pre-testing apparatus, the degree of physical property deterioration of the sample was examined due to repetitive folding operations at a bend angle of 180°.

EXAMPLE 6

Sample: Polypropylene sheet (Grade: RB-110 made by Tokuyama Soda Co., Ltd.). The thickness is 0.2 mm. (Reference color: Y=65.5, x=0.312, y=0.316)

Result and comparison: As shown in Table 7.

TABLE 7

| Formal testing machine | | Pre-testing apparatus | |
|---|---|---|---|
| Irradiation time (hours) | Degree of deterioration* | Irradiation time (hours) | Degree of deterioration* |
| 100 | A | 10 | A |
| 200 | A | 20 | A |
| 300 | B | 30 | B |
| 500 | C | 40 | C |
|  |  | 50 | C |

*A: The sample was not cut even when it had been folded 50 times or more.
B: The sample was cut when it had been folded 20 times or more.
C: The sample was cut when it had been folded once.

(B-2) Tensile impact test

The est was performed on the basis of ASTMD1822 using the universal impact testing machine made by Toyo Seiki Mfg. Co., Ltd. The ratios of the times regarding formal testing machine and pre-testing apparatus were obtained in a similar manner as in case of the color difference. Then, the acceleration properties (magnifications) of the ultraviolet deterioration were derived.

EXAMPLE 7

Sample: Acrylic denaturation PVC sheet (Trade name: Daipla AV sheet). The thickness is 3.0 mm.

Figure 10A:
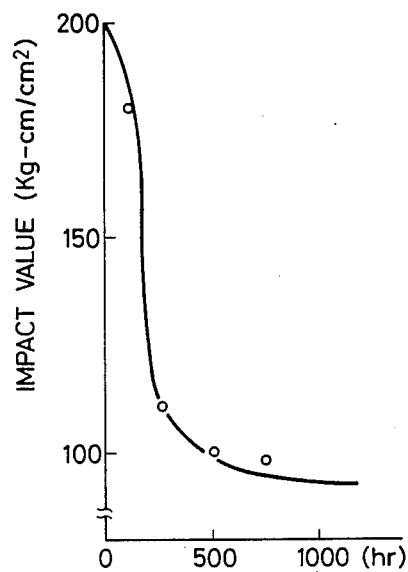
Figure 10B:
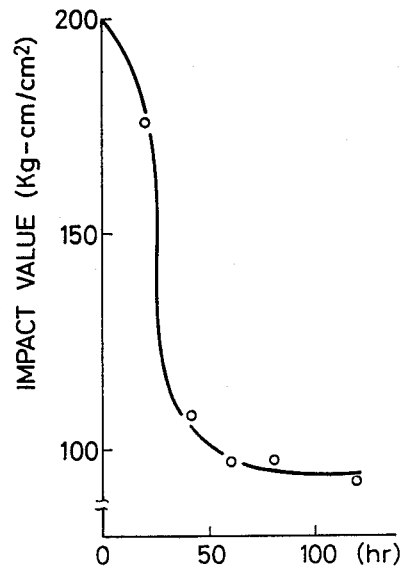

Result: In case of the formal testing machine .... As shown in FIG. 10A. In case of the pre-testing apparatus .... As shown in FIG. 10B.

Comparison: As shown in Table 7 (mean magnification: 7.8)

TABLE 8

| Impact value (kg-cm/cm²) | Formal testing machine R (hours) | Pre-testing apparatus P (hours) | R/P |
|---|---|---|---|
| 180 | 120 | 20 | 6.0 |
| 150 | 160 | 26 | 6.2 |
| 110 | 270 | 34 | 8.0 |
| 95 | 700 | 65 | 10.8 |

(Mean: 7.8)

As will be obvious from the data in Examples 6 and 7, the use of the pre-testing method according to the present invention also enables the data regarding the ultraviolet deterioration on the physical property surface of the sample to be obtained in an extremely short time as compared with the case where the formal testing machine was used.

What is claimed is:

1. Apparatus for weather-testing a sample, comprising:
    a high pressure radiation-generating metal vapor discharge lamp, said lamp being a metal halide lamp having mainly halide of iron enclosed in a lamp tube together with mercury and rare gas;
    filter means surrounding the lamp for removing, from radiation generated by the lamp, wavelength components other than ultraviolet wavelength components included in sunlight incident on the earth's surface, said filter means substantially removing wavelength components other than ultraviolet wavelength components in the wavelength range of 290–460 nm from radiation generated by said lamp;
    a cooling jacket surrounding the lamp and having a transparent inner tube and an outer tube transparent at least to said ultraviolet wavelength components, said inner tube being separated from an outer surface of said lamp tube by an air gap, said outer tube being spaced from said inner tube, with said filter means disposed in the space between said inner and outer tubes, said space being isolated from said lamp, said cooling jacket having inlet and outlet means for providing a stream of liquid through said space for cooling said filter means;
    means for mounting the sample to expose the sample to ultraviolet radiation transmitted through said filter means from said lamp and with an ultraviolet radiation intensity incident on said sample of at least 50 mW/cm²;
    means for blowing air onto said sample for cooling said sample to a temperature maintained below 80° C. while said sample is irradiated by said ultraviolet radiation; and
    a closed chamber enclosing at least the lamp, the sample mounting means, the sample, the filter means, and the cooling jacket and forming a closed environment wherein the sample is weather-tested.

2. Apparatus according to claim 1, wherein said filter means is made of a low melting point glass.

3. Apparatus according to claim 1, wherein said cooling liquid is water.

4. Apparatus according to claim 1, wherein said sample mounting means includes means for adjusting the distance between said sample and said lamp.

5. Apparatus according to claim 1, further comprising a reflector for reflecting radiation generated by said lamp toward said sample.

6. Apparatus according to claim 1, wherein the intensity of the ultraviolet radiation incident on said sample is between 80 and 120 mW/cm², and wherein said means for blowing air onto said sample maintains the temperature of said sample at 65° C. or less.

* * * * *